United States Patent
Loetjoenen et al.

(10) Patent No.: US 10,372,786 B2
(45) Date of Patent: Aug. 6, 2019

(54) STATE INFERENCE IN A HETEROGENEOUS SYSTEM

(71) Applicant: Combinostics Oy, Tampere (FI)

(72) Inventors: Jyrki Loetjoenen, Tampere (FI); Juha Koikkalainen, Tampere (FI); Jussi Mattila, Tampere (FI)

(73) Assignee: Combinostics Oy, Tampere (FI)

( * ) Notice: Subject to any disclaimer, the term of this patent is extended or adjusted under 35 U.S.C. 154(b) by 97 days.

(21) Appl. No.: 15/430,129

(22) Filed: Feb. 10, 2017

(65) Prior Publication Data

US 2017/0169352 A1    Jun. 15, 2017

Related U.S. Application Data

(63) Continuation of application No. 13/806,679, filed as application No. PCT/FI2010/050545 on Jun. 24, 2010, now abandoned.

(51) Int. Cl.
*G06F 17/00* (2019.01)
*G06F 7/24* (2006.01)
(Continued)

(52) U.S. Cl.
CPC ............... *G06F 17/00* (2013.01); *G06F 7/24* (2013.01); *G06F 16/9027* (2019.01);
(Continued)

(58) Field of Classification Search
CPC .... G06F 17/00; G06F 17/30961; G06F 17/18; G06F 17/30; G06N 7/005
(Continued)

(56) References Cited

U.S. PATENT DOCUMENTS 7,383,470 B2    6/2008   Canning et al.
8,081,088 B2   12/2011   Clausner et al.
(Continued)

FOREIGN PATENT DOCUMENTS

EP    1552311 B1   11/2008
EP    1725876 B1    5/2009
(Continued)

OTHER PUBLICATIONS

European Patent Office, Extended European Search Report for Application No. 10853566.7, dated Nov. 20, 2014, 8 pages, Germany.
(Continued)

*Primary Examiner* — John E Breene
*Assistant Examiner* — Jeffrey P Aiello
(74) *Attorney, Agent, or Firm* — Alston & Bird LLP

(57) ABSTRACT

The invention relates to inferring the state of a system of interest having a plurality of indicator values and possibly being heterogeneous in nature. A number of indicator values from a control state and from a comparison state are gathered. From these indicator values, classification power between the control and comparison states (measure of goodness) is computed. Difference values are computed for the indicator values from the system of interest based on the difference to the indicator values from control and comparison states. From a number of these indicators, composite indicators are formed, and composite measures of goodness and composite difference values are computed. A plurality of composite indicators may be formed at different levels. These indicators may be represented as a tree and grouped according to content, and at the same time they may be arranged according to the measure of goodness or some other value. The indicators, measures of goodness, and difference values may be visualized and shown to a user,
(Continued)

who may use such a representation for inferring the state of the system.

24 Claims, 11 Drawing Sheets

(51) Int. Cl.
G06N 7/00 (2006.01)
G16H 50/30 (2018.01)
G16H 50/20 (2018.01)
G06F 16/901 (2019.01)
G06K 9/62 (2006.01)
G06F 17/18 (2006.01)
G06F 19/00 (2018.01)

(52) U.S. Cl.
CPC ............. *G06F 17/18* (2013.01); *G06F 19/00* (2013.01); *G06K 9/6253* (2013.01); *G06K 9/6265* (2013.01); *G06K 9/6296* (2013.01); *G06N 7/005* (2013.01); *G16H 50/20* (2018.01); *G16H 50/30* (2018.01)

(58) Field of Classification Search
USPC .................................. 702/179, 181; 706/52
See application file for complete search history.

(56) References Cited

U.S. PATENT DOCUMENTS

| | | |
|---|---|---|
| 2003/0219797 A1 | 11/2003 | Zhao et al. |
| 2004/0019456 A1 | 1/2004 | Circenis |
| 2004/0073096 A1 | 4/2004 | Kates et al. |
| 2004/0267770 A1* | 12/2004 | Lee .................. G06F 17/30539 |
| 2005/0288802 A1 | 12/2005 | Yamada |
| 2006/0047478 A1 | 3/2006 | Di Palma et al. |
| 2006/0150169 A1* | 7/2006 | Cook ........................ G06F 8/10 717/156 |
| 2007/0239636 A1* | 10/2007 | Tang ....................... G06N 7/005 706/20 |
| 2007/0271209 A1* | 11/2007 | Koikkalainen ...... G06K 9/6253 706/52 |
| 2008/0010225 A1* | 1/2008 | Gonsalves ............. G06N 7/005 706/11 |
| 2008/0140473 A1* | 6/2008 | Taylor .................... G06Q 10/06 705/7.28 |
| 2009/0100293 A1 | 4/2009 | LaComb et al. |
| 2009/0167763 A1* | 7/2009 | Waechter ................ G06T 15/06 345/426 |
| 2009/0281735 A1 | 11/2009 | Bechhoefer |
| 2010/0153321 A1* | 6/2010 | Savvides ............... G06F 17/271 706/13 |
| 2011/0069072 A1 | 3/2011 | Nakano |
| 2011/0225548 A1* | 9/2011 | Callens ................. G06F 3/0481 715/835 |
| 2011/0238613 A1* | 9/2011 | Shehory .............. G06F 11/3664 706/52 |
| 2011/0251513 A1 | 10/2011 | Chetham et al. |
| 2011/0301489 A1 | 12/2011 | Essex et al. |
| 2012/0185424 A1* | 7/2012 | Vaidyanathan ........ G06N 7/005 706/52 |
| 2013/0096878 A1 | 4/2013 | Lotjonen et al. |

FOREIGN PATENT DOCUMENTS

| | | |
|---|---|---|
| WO | WO 2007/132066 A2 | 11/2007 |
| WO | WO 2013/121107 A2 | 8/2013 |

OTHER PUBLICATIONS

Gooley, Ted A., et al., "Estimation of Failure Probabilities in Presence of Competing Risks: New Representations of Old Estimators," Statistics in Medicine, 1999, pp. 695-706, vol. 18, John Wiley & Sons, Ltd., USA.

International Preliminary Examining Authority, International Preliminary Report on Patentability for International Application No. PCT/FI2010/050545 and Applicant's Apr. 13, 2012 Response to the International Preliminary Examining Authority's Written Opinion dated Apr. 28, 2011, dated Nov. 8, 2012, 30 pages, National Board of Patents and Registration of Finland, Finland.

International Preliminary Examining Authority, Written Opinion for International Application No. PCT/FI2010/050545, dated Jun. 4, 2012, 8 pages, National Board of Patents and Registration of Finland, Finland.

International Searching Authority, International Search Report for International Application No. PCT/FI2010/050545, dated Apr. 28, 2011, 6 pages, National Board of Patents and Registration of Finland, Finland.

International Searching Authority, Written Opinion for International Application No. PCT/FI2010/050545, dated Apr. 28, 2011, 10 pages, National Board of Patents and Registration of Finland, Finland.

Nardo, Michela, et al., "Tools for Composite Indicators Building," [Retrieved on Apr. 13, 2011], Retrieved from the Internet: <URL:http://composite-indicators.jrc.ec.europa.eu/articles_books.htm>, 134 pages, European Communities, 2005, European Union.

Salas-Gonzales, D., et al., "Computer-Aided Diagnosis of Alzheimer's Disease Using Support Vector Machines and Classification Trees," Physics in Medicine and Biology, May 21, 2010, pp. 2807-2817, vol. 55, [Retrieved on Apr. 21, 2011], Retrieved from the Internet: <URL:http://iopscience.iop.org/0031-9155/55/10/002/>, IOP Publishing, UK.

United States Patent and Trademark Office, Office Action for U.S. Appl. No. 13/806,679, dated Jul. 6, 2015, 17 pages, U.S.A.

United States Patent and Trademark Office, Office Action for U.S. Appl. No. 13/806,679, dated Feb. 9, 2016, 15 pages, U.S.A.

United States Patent and Trademark Office, Office Action for U.S. Appl. No. 13/806,679, dated Jul. 14, 2016, 26 pages, U.S.A.

United States Patent and Trademark Office, Office Action for U.S. Appl. No. 13/806,679, dated Nov. 22, 2016, 18 pages, U.S.A.

* cited by examiner

☐ 0,33 - Neuropsychological Tests
◨ 0,41 - Genetic Tests
◨ 0,87 - Imaging
◨ 0,91 - Molecular Tests

STATE INFERENCE IN A HETEROGENEOUS SYSTEM

CROSS-REFERENCE TO RELATED APPLICATIONS

This application is a continuation of and claims priority to and the benefit of U.S. Nonprovisional patent application Ser. No. 13/806,679, filed Dec. 21, 2012, which is a national stage application, filed under 35 U.S.C. § 371, of International Application No. PCT/FI2010/050545, filed Jun. 24, 2010, the contents of both of which as are hereby incorporated by reference in their entirety.

BACKGROUND

The invention relates to a method of inferring the state of a system and classifying data. The invention relates to an apparatus and a system for inferring the state of a system and visualizing the state. The invention relates to the computer program product for inferring the state of a system and visualizing the state.

Any arbitrary system of interest can have at least two states. The system of interest can be, for example, an apparatus, a human body, or a financial entity. Typically, the system of interest either functions correctly (normal state) or has a malfunction (error state). There may be several normal and/or error states. A good example is the healthiness of a human being: he or she can be healthy (normal state) or have a disease (error state), in which case the number of the error states may be large. The state of the system of interest defines which normal or error state the system of interest is in and how much the state of the system of interest differs from a control state specified beforehand. For example, in medical applications the state of the system of interest defines the disease a patient has and how far the disease has advanced, as compared with the normal, healthy state. In industrial applications the state of the system of interest defines the malfunction of an apparatus and how severe the malfunction is.

Computerized methods are needed in the above-mentioned analyses of the systems of interest to efficiently utilize multidimensional data and to find complex relations in the data. Each dimension of the data relates to an aspect of the particular system that is being measured (i.e. an indicator) and from which measurement values (indicator values) are gathered. Typically, the computerized methods give only a classification (normal/error) as an output. However, in many applications the computerized methods cannot make the final decision because of possible erroneous measurements and uncertainty in the data, or merely because the computer cannot fully mimic the knowledge and experience of an expert. In such cases, a human user needs to make the final decision.

Nowadays, there is typically a large number of data available to the user interpreting the state of a system of interest. For example, different signals and images measured and results of various tests may be available for the user to inspect. Some of these values and pieces of information may have additional information on the normal range of the value, and the user needs to observe this range in addition to the value itself. The different values and data may be at least partially conflicting, and the data may be heterogeneous so that combining the data heuristically or numerically may be difficult and unreliable. Determining the state of the system may therefore be very time-consuming and prone to errors in interpretation.

There is, therefore, a need for solutions that make it faster, easier and less prone to errors to infer a state of a system from heterogeneous information.

BRIEF SUMMARY

Now there has been invented an improved method and technical equipment implementing the method, by which the above problems are alleviated. Various aspects of the invention include a method, an apparatus, a server, a client and a computer readable medium comprising a computer program stored therein, which are characterized by what is stated in the independent claims. Various embodiments of the invention are disclosed in the dependent claims.

According to a first aspect of the invention, there is provided a method, comprising defining a first indicator and a second indicator in a system, the values of the first indicator and the second indicator being indicative of the state of the system of interest, forming a measure of goodness for said first indicator and for said second indicator by using values of said first indicator and values of said second indicator, respectively, of a control state and a comparison state, forming a difference value for said first indicator and for said second indicator in a system of interest with reference to said first and second indicators in said control and comparison states, defining a composite indicator of said first indicator and said second indicator, forming a measure of goodness for the composite indicator by using information indicative of said measure of goodness of said first indicator and said second indicator, forming a difference value for the composite indicator in a system of interest, and arranging said composite indicator to be used in inferring the state of the system of interest.

According to an embodiment, the method further comprises forming said difference values for said first and second indicators to be indicative of whether the system of interest is in a control state or a comparison state or in a state between the control state and the comparison state, and displaying difference values arranged according to their respective measures of goodness for inferring the state of the system of interest. According to an embodiment, the method further comprises displaying said difference values of said first, second and composite indicators of said system of interest to a user, wherein said difference values of said first, second and composite indicators of said system of interest are displayed with a value such as a number, a symbol, a color, a shade, a pattern, a bar or a gauge, and said difference values of said first, second and composite indicators are highlighted and/or suppressed according to the respective measure of goodness of said first, second and composite indicators using a visual cue such as size, blinking, position on the display or stacking. According to an embodiment, the method further comprises displaying said difference value of said composite indicator of said system of interest with a colour symbol on a first level in a tree structure, displaying said difference values of said first and second indicator of said system of interest with a colour symbol on a second level in a tree structure, displaying said measures of goodness of said first, second and composite indicators of said system of interest with a size of said colour symbol. According to an embodiment, the method further comprises grouping said tree structure by forming groups of indicators that are on the same level of the tree and that are linked to a composite indicator of another level, and arranging said groups of said tree structure according to said measures of goodness so that indicators having a larger measure of goodness are arranged to appear visually together. According to an embodiment, the method further comprises arranging said groups of indicators to appear horizontally in a decreasing order according to the respective measures of goodness of the composite indicators, and arranging indicators inside said groups of indicators to appear vertically in a decreasing order according to their respective measures of goodness. According to an embodiment, the method further comprises computing the difference value of said composite indicator of said system of interest from the difference values of said first and second indicator of said system of interest, the calculation being done according to the respective measures of goodness of said first and second indicator of said system of interest, such as using a weighted average. According to an embodiment, the method further comprises computing the measures of goodness of said first, second and composite indicators by determining a statistical probability of said indicator being a reliable measure for determining whether the said system of interest belongs to said at least one control or comparison state. According to an embodiment, the method further comprises computing the measure of goodness of said composite indicator of said system of interest using attributes of said first and second indicators of said system of interest in the calculation. According to an embodiment, the method further comprises computing at least one said difference value by comparing an indicator of said system of interest to indicators of at least one control and comparison state, and computing at least one said measure of goodness by using a statistical distribution of said at least one control and comparison state.

According to a second aspect of the invention, there is provided an apparatus comprising at least one processor and memory including computer program code, the memory and the computer program code configured to define a first indicator and a second indicator in a system, the values of the first indicator and the second indicator being indicative of the state of the system of interest, form a measure of goodness for said first indicator and for said second indicator by using values of said first indicator and values of said second indicator, respectively, of a control state and a comparison state, form a difference value for said first indicator and for said second indicator in a system of interest with reference to said first and second indicators in said control and comparison states, define a composite indicator of said first indicator and said second indicator, form a measure of goodness for the composite indicator by using information indicative of said measure of goodness of said first indicator and said second indicator, form a difference value for the composite indicator in a system of interest, and arrange said composite indicator to be used in inferring the state of the system of interest.

According to an embodiment, the apparatus further comprises computer program code configured to form said difference values for said first and second indicators to be indicative of whether the system of interest is in a control state or a comparison state or in a state between the control state and the comparison state, and display difference values arranged according to their respective measures of goodness for inferring the state of the system of interest. According to an embodiment, the apparatus further comprises computer program code configured to display said difference values of said first, second and composite indicators of said system of interest to a user, wherein said difference values of said first, second and composite indicators of said system of interest are displayed with a value such as a number, a symbol, a color, a shade, a pattern, a bar or a gauge, and said difference values of said first, second and composite indicators are highlighted and/or suppressed according to the respective measure of goodness of said first, second and composite indicators using a visual cue such as size, blinking, position on the display or stacking. According to an embodiment, the apparatus further comprises computer program code configured to display said difference value of said composite indicator of said system of interest with a colour symbol on a first level in a tree structure, display said difference values of said first and second indicator of said system of interest with a colour symbol on a second level in a tree structure, and display said measures of goodness of said first, second and composite indicators of said system of interest with a size of said colour symbol. According to an embodiment, the apparatus further comprises computer program code configured to group said tree structure by forming groups of indicators that are on the same level of the tree and that are linked to a composite indicator of another level, and arrange said groups of said tree structure according to said measures of goodness so that indicators having a larger measure of goodness are arranged to appear visually together. According to an embodiment, the apparatus further comprises computer program code configured to arrange said groups of indicators to appear horizontally in a decreasing order according to the respective measures of goodness of the composite indicators, and arrange indicators inside said groups of indicators to appear vertically in a decreasing order according to their respective measures of goodness. According to an embodiment, the apparatus further comprises computer program code configured to compute the difference value of said composite indicator of said system of interest from the difference values of said first and second indicator of said system of interest, the calculation being done according to the respective measures of goodness of said first and second indicator of said system of interest, such as using a weighted average. According to an embodiment, the apparatus further comprises computer program code configured to compute the measures of goodness of said first, second and composite indicators by determining a statistical probability of said indicator being a reliable measure for determining whether the said system of interest belongs to said at least one control or comparison state. According to an embodiment, the apparatus further comprises computer program code configured to compute the measure of goodness of said composite indicator of said system of interest using attributes of said first and second indicators of said system of interest in the calculation. According to an embodiment, the apparatus further comprises computer program code configured to compute at least one said difference value by comparing an indicator of said system of interest to indicators of at least one control and comparison state, and compute at least one said measure of goodness by using a statistical distribution of said at least one control and comparison state.

According to a third aspect of the invention, there is provided a system comprising at least one processor, memory including computer program code, the memory and the computer program code configured to define a first indicator and a second indicator in a system, the values of the first indicator and the second indicator being indicative of the state of the system of interest, form a measure of goodness for said first indicator and for said second indicator by using values of said first indicator and values of said second indicator, respectively, of a control state and a comparison state, form a difference value for said first indicator and for said second indicator in a system of interest with reference to said first and second indicators in said control and comparison states, define a composite indicator of said first indicator and said second indicator, form a measure of goodness for the composite indicator by using information indicative of said measure of goodness of said first indicator and said second indicator, form a difference value for the composite indicator in a system of interest, and arrange said composite indicator to be used in inferring the state of the system of interest.

According to an embodiment, the system further comprises computer program code configured to form said difference values for said first and second indicators to be indicative of whether the system of interest is in a control state or a comparison state or in a state between the control state and the comparison state, and display difference values arranged according to their respective measures of goodness for inferring the state of the system of interest.

According to a fourth aspect of the invention, there is provided a computer program product stored on a computer readable medium and executable in a data processing device, the computer program product comprising a computer program code section for defining a first indicator and a second indicator in a system, the values of the first indicator and the second indicator being indicative of the state of the system of interest, a computer program code section for forming a measure of goodness for said first indicator and for said second indicator by using values of said first indicator and values of said second indicator, respectively, of a control state and a comparison state, a computer program code section for forming a difference value for said first indicator and for said second indicator in a system of interest with reference to said first and second indicators in said control and comparison states, a computer program code section for defining a composite indicator of said first indicator and said second indicator, a computer program code section for forming a measure of goodness for the composite indicator by using information indicative of said measure of goodness of said first indicator and said second indicator, a computer program code section for forming a difference value for the composite indicator in a system of interest, and a computer program code section for arranging said composite indicator to be used in inferring the state of the system of interest.

According to an embodiment, the computer program product further comprises a computer program code section for forming said difference values for said first and second indicators to be indicative of whether the system of interest is in a control state or a comparison state or in a state between the control state and the comparison state, and a computer program code section for displaying difference values arranged according to their respective measures of goodness for inferring the state of the system of interest.

BRIEF DESCRIPTION OF THE SEVERAL VIEWS OF THE DRAWING(S)

In the following, various embodiments of the invention will be described in more detail with reference to the appended drawings, in which FIG. 1 shows a method for inferring the state of a system of interest according to an example embodiment of the invention;

DETAILED DESCRIPTION OF VARIOUS EMBODIMENTS

It has been noticed in the invention that databases of complex systems comprising heterogeneous data, such as medical records, population demographics, and process analysis data, often contain information that is not immediately obvious to the observer. It has also been noticed in the invention that there may be a need for novel decision support systems utilizing heterogeneous data in a plethora of environments, such as medicine, financing, and manufacturing. Such environments would benefit from a solution like the present invention to analyze available data and visualize analysis results for quick understanding of the parameters in question. The present invention provides methods for analyzing and visualizing statistical aspects of heterogeneous datasets, allowing quick inspection and state inference by field experts. The visualization methods may be useful in several fields as decision support systems, and they may also be used as a data mining tool for research. Further, it has been noticed that data mining is a hot topic in several data-intensive fields, and many of them would benefit from visual analysis of heterogeneous data.

The present invention may offer, among other embodiments, a hierarchical data visualization method for heterogeneous feature values based on statistical properties of the data. In a set of related databases, information that can be quantified and represented as indicators (indicator values can be e.g. numeric values, classifying values, and free text using text mining methods) may be used for building two or more classes representing divergent states of a system. Based on classification criteria, one of these may be chosen to be a control state and the rest may be comparison states. Indicator values belonging to comparison states may be compared statistically to the indicator values of the control state to find statistical differences between the states and also the statistical significance of the difference. Indicators may be organized in a hierarchy for visualization where the expert may more easily see which indicator values diverge between the states and how significant and reliable this difference is in classifying among the states. In addition to control and comparison state differences, a single system of interest may be compared to the control and comparison states for inferring its state, i.e. to discover indicator values, probabilities, or other measures that are reflecting the belonging of the system of interest to different control and comparison states.

Figure 1:
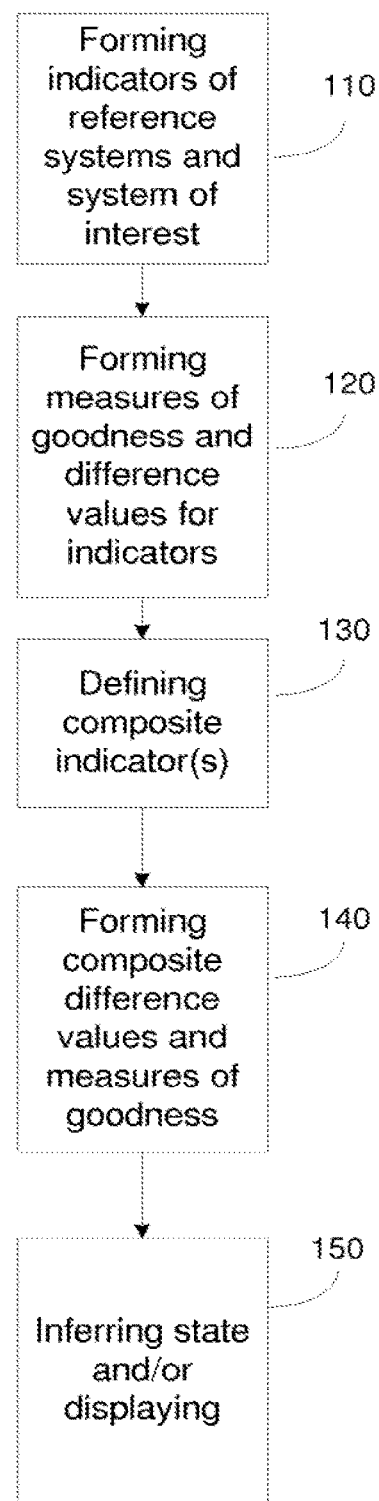

FIG. 1 shows a method for inferring the state of a system according to an example embodiment of the invention. The invention infers the state of a system of interest from a set of indicators determined or measured from the system of interest. The analysis may be carried out by comparing data from the system of interest with the data in the databases of at least one control state (e.g. a normal state) and a comparison state (e.g. a error state) using statistical methods. The database of a state includes data from at least one example of a system that is known to be in a particular state. One state, either a real or a synthetic state, may be selected as a control state. For example, if the system is a human brain and one control state is a healthy state, the database of the healthy state contains measurement values (i.e. indicator values) from at least one healthy brain describing, for example, the anatomy and function of the healthy brain. Another comparison state, an error state, may be a brain disease, and the database of the comparison state contains measurement values from at least one person with the brain disease. The databases may also be a single database which includes all available information for all states pertaining to the context. For the clarity of description, we use the term 'database' for denoting both a single database containing all information about all states and several databases containing this information as entirety.

In phase 110, indicator values for the control state and the comparison states are retrieved from the database using the different data available for the states. In phase 120, measures of goodness for control and comparison states and difference values for the indicator values of a system of interest are formed. The measure of goodness indicates, as an index number, how significant or reliable the indicator is in differentiating between control and comparison states. The measure of goodness is defined from data available in the database about the control and comparison states, i.e., the measures of goodness may be independent on the indicator values defined for the system of interest being studied. The difference value indicates, with regard to the indicator, the distance of the system of interest from the control and one or more comparison states, or may indicate a relative distance of the system of interest between control and comparison states, or may indicate probabilities of whether the system of interest belongs to control or comparison states. In other words, a difference value gives indication to how probable it is that the system of interest is in a particular control or comparison state. The difference value, or other computed values, may also describe how distinct the state of the system of interest is.

In phase 130, at least one composite indicator is defined. The defining may practically happen by grouping a number of indicators and defining a composite indicator for that group. There may be a number of composite indicators defined in such manner. An indicator may be associated with only one composite indicator, or an indicator may be associated with two or more composite indicators. The composite indicators may in turn be grouped and combined with other composite and non-composite indicators to form new composite indicators, thereby forming a multi-level structure such as a tree or a network.

In phase 140, measures of goodness for the composite indicators and/or composite difference values for the system of interest are formed. The measure of goodness of a composite indicator may be formed or computed by using the statistical properties of some or all of the indicator values contained in the composite indicator, or it may be derived from the measures of goodness of the indicators from which the composite indicator is derived, or both. The composite difference values may be formed or computed, e.g. by combining the difference values of the relevant indicators or by computing it from scratch using all the relevant indicator values e.g. using probabilistic or statistical computation. Combining of the difference values may also happen in a weighted manner by weighting the difference values of the relevant indicators with the measures of goodness, or the combining may happen without using the measures of goodness at all. Indicator values for the composite indicators may also be formed by using the difference values and the measures of goodness and the composite difference values and measures of goodness may be then computed from these composite indicators.

In phase 150, by using the original indicators and/or the composite indicators, the state of the system of interest is inferred. This may happen automatically by computing, or semi-automatically so that the indicators and the composite indicators are displayed appropriately to the user so that he/she can determine the state of the system of interest. Indicators may be displayed in a hierarchical manner and may be ordered to offer insight for inference and to emphasize measures of goodness and/or difference values. In this phase, the difference values and the measures of goodness may be used for inferring the state, be they the original difference values and measures of goodness or composite difference values and measures of goodness.

Figure 2A:
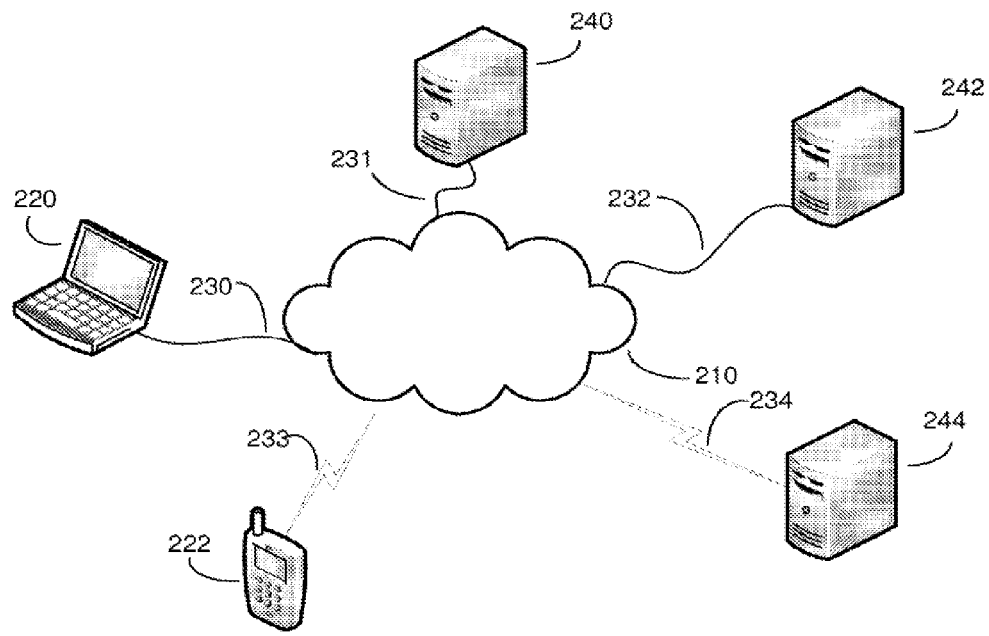
FIGS. 2a and 2b show devices and a system arranged to infer and/or display the state of a system of interest according to an example embodiment of the invention.

In the following, several further embodiments of the invention will be described in the context of determining the state of a human being. It is to be noted, however, that the invention is not limited to be applied to human beings and such. In fact, the different embodiments have applications widely in any environment where improvements in inferring the state of a complex system and/or visualizing the same are required. For example, systems dealing with complex data such as financial data, geological data, or atmospheric data may benefit from the use of the invention. Likewise, various control systems may benefit from the invention, for example those associated with controlling an industrial process. Also, authorities may use the invention e.g. for determining demographic profiles. For the remainder of this document we will use an example dataset to clarify some aspects of the invention. As was mentioned, the invention is not limited to the following example dataset. Let us consider a database containing medical data about patients who have been suspected or confirmed of having Alzheimer's disease (AD). Information in the database contains patient information (name, age, etc.), patient demographics information (years of education, occupation), Alzheimer's disease diagnoses, neuropsychological test results, magnetic resonance imaging (MRI) images of the brain with quantification results (e.g., region volumes), and AD biomarker information from cerebrospinal fluid (CSF) samples. We consider as a system of interest a person who comes to a memory clinic after his family has noticed problems in daily life due to mild memory problems. FIG. 2a shows devices and a system arranged to infer and/or display the state of a system according to an example embodiment of the invention. The different devices are connected via a network 210 such as the Internet or a local area network or any wired or wireless communication network. There are a number of servers connected to the network 210, and here are shown a server 240 for offering a network service e.g. for classifying a system, a server 242 for storing datasets related to the service and a server 244 for processing data and performing computations. These servers may be made of multiple parts or they may be combined into one more servers.

There are also a number of end-user devices such as personal computers 220 and mobile phones 222. These devices 220 and 222 may also be made of multiple parts. The various devices are connected to the network 210 via communication connections such as a fixed connection 230, 231 and 232 or a wireless connection 233 and 234. The connections may be implemented by means of communication interfaces at the respective ends of the communication connection.

The various embodiments of the invention may be implemented with the help of computer program code that resides in a memory and causes the relevant apparatuses to carry out the invention. For example, a personal computer may comprise circuitry and electronics for handling, receiving and transmitting data, computer program code in a memory, and a processor that, when running the computer program code, causes the computer to carry out the features of an embodiment. Yet further, a server may comprise circuitry and electronics for handling, receiving and transmitting data, computer program code in a memory, and a processor that, when running the computer program code, causes the server to carry out some or all of the features of an embodiment.

Figure 2B:
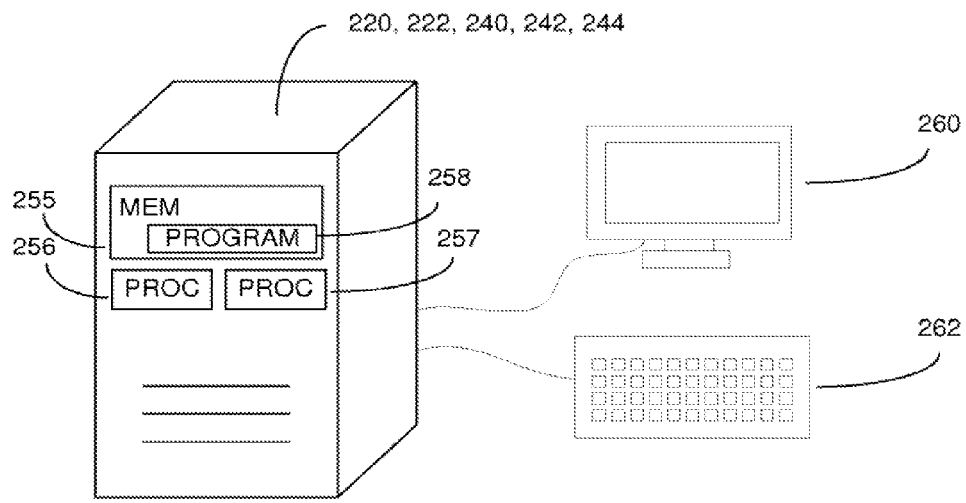

FIG. 2b shows a device arranged to infer and/or display the state of a system according to an example embodiment. As shown in FIG. 2b, the device 220, 222, 240, 242 or 244 contains memory 255, one or more processors 256, 257, and computer program code 258 residing in the memory 255 for implementing, for example, computations for inferring the state of the system. The device may also be functionally connected to a display 260 for example for displaying the system indicators according to an embodiment. There may also be various input means functionally connected to the device, such as a keyboard 262, speech command interface, data gloves, and different communication interfaces for receiving input (not shown).

It needs to be understood that different embodiments allow different parts to be carried out in different elements. For example, storing the data sets, forming the indicators and displaying the indicators may be carried out entirely in one device or across multiple devices. For example, data may be stored in one device, the user input may be received by another device, and the computations may be carried out in a third device. The various functions of the invention may be implemented as a software component residing on one device or distributed across several devices. A doctor in a hospital may use an embodiment running on the doctor's personal computer, connected to the hospital information system (HIS), drawing data from several servers in the hospital, e.g. a image server and a clinical investigations data server, and computing analyses locally. Another embodiment may be a web browser based solution remotely accessed over the Internet, where the system of interest is described by a user entering indicators in a web form which would then perform data retrieval from some server, data analysis on another, and visualization of the results inside the web application.

There may be several phases to the invention. Such phases may be 1) indicator value sampling (i.e. forming of control and comparison states from available data), 2) indicator value analysis (i.e. computing measures of goodness for indicators and/or difference values for the system of interest), 3) forming composite indicators in a tree hierarchy (i.e. combining indicators and computing the composite measures of goodness), 4) determining the state of the system of interest (i.e. computing its composite difference values) 5) feature re-ordering for visualization (e.g. based on the measures of goodness), and 6) dynamic refinement of the visualization (e.g. due to new available data or user interaction). These phases are described later in context with the respective example embodiments.

Sampling is the process of forming control and comparison states from available data. It should be noted that the selected states need not be exclusively the control state and the comparison state. Depending on the goals of the analysis and the sets of measurements, the states may be named in a different manner, e.g. state 1, state 2 etc. These states may correspond to the control state and to the comparison state, or not. The data used for constructing the states may be sparse, meaning that we may not have exhaustive collections of data or test results from all possible time points and/or measurable indicators. We may only have information that has been collected successfully. This issue may be taken into account during sampling, e.g. some indicators may be pruned from the analyses since not enough data exists.

There are several ways to do sampling (i.e. extracting data) from databases to form states. The following list includes some solutions for forming a state but is not exhaustive. 1) Take all data based on some criteria. 2) Take enough of data based on some criteria. 3) Stratified selection (i.e. choose data with some criteria that also matches a profile similar to the system of interest). In our example case, stratified sampling of states may be done by taking data of all patients who are of the same age and had a similar degree of education when they were initially admitted for studies as our system of interest. From this data two states may be formed, one from those who were eventually diagnosed with Alzheimer's disease (i.e. comparison state) and the other from those who were healthy (i.e. control state). 4) Take the examples that differ most from another state. This can be done using Cartesian distance, Mahalanobis distance, or statistical tests. The number of indicator values selected for the states can be defined using a constant number, or a threshold for the distances or the results of the statistical tests. The outliers may also be detected and removed from the states. 5) Generate one synthetic collection of indicator values that represents the worst case of the state in comparison to another state. For each measurement, the N extreme indicator values are searched. The largest values are searched if the indicator values of the state are larger than the values of a comparison state, and respectively the smallest values are searched if the indicator values in the state are smaller than in the comparison state. In addition to these, other sampling schemes may be used.

Figure 3:
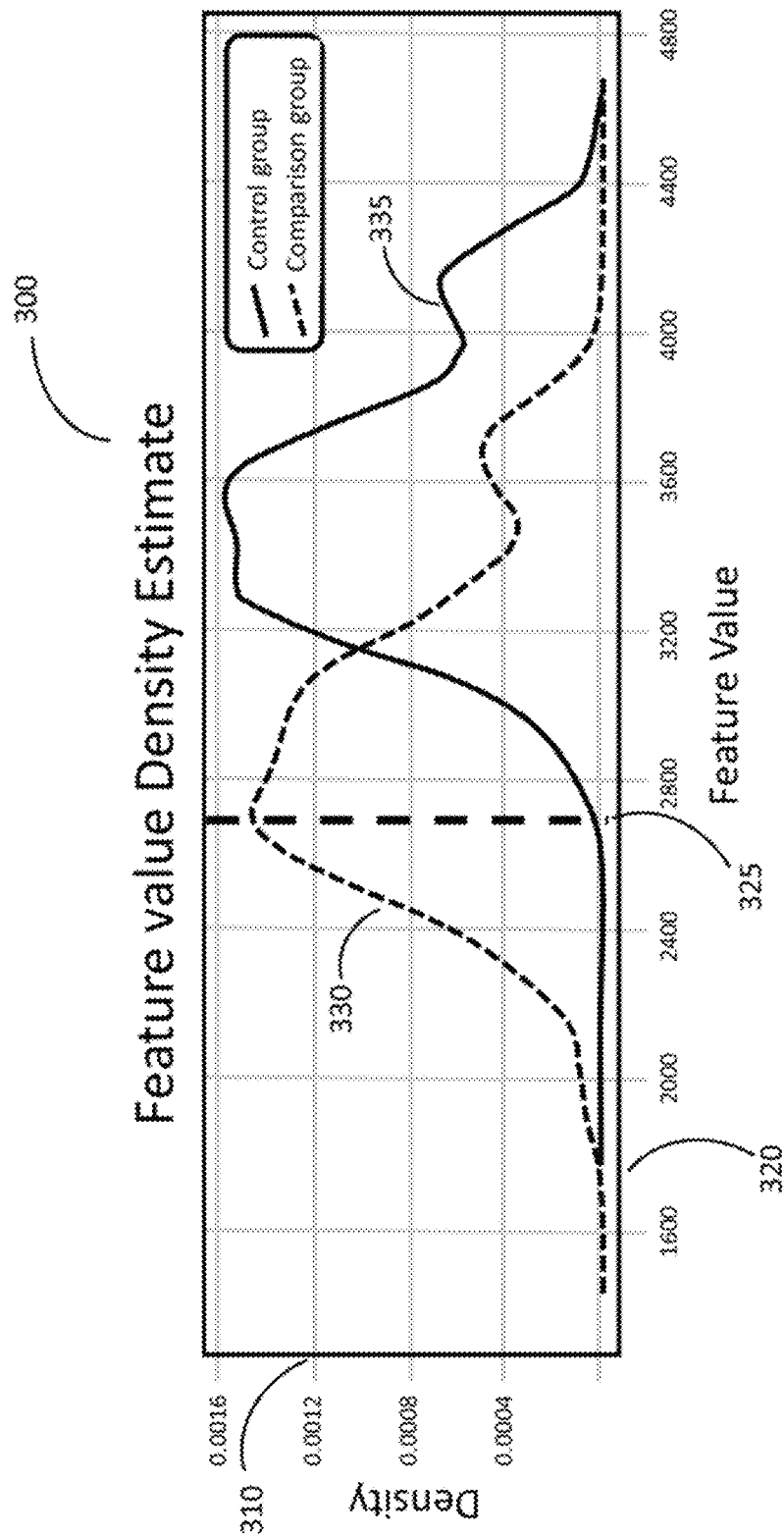
FIG. 3 shows a representation and visualization of probability distributions for a control and comparison state and illustrates visualization of the state of the system of interest according to an example embodiment.

FIG. 3 shows one indicator after sampling using a representation of probability distributions for control and comparison groups. It also illustrates visualization of an indicator from a system of interest according to an example embodiment. This information about a sampled indicator and its distribution may be shown to the user e.g. as a graph 300. In FIG. 3, density estimates 330 and 335 are shown. These density estimates indicate an estimated probability density 310 of a indicator 320. In other words, if a certain indicator value 320 has a high density value 310 according to the density function, the indicator value 320 is likely to appear in data. If the value is low, it is less likely that such a value for the indicator would appear. Accordingly, the shapes of the density functions 330 and 335 indicate which values are more probable for the control and comparison states. For example, it is clearly more likely that an indicator value from a system of interest 325 of approximately 2700 would belong to the comparison state than the control state. Measure of goodness and difference value for the indicator in question may be determined from the data used in the visualization by e.g. distance measure or probabilistic measure as defined below.

During sampling we constructed two or more states which include some or all available indicators (and indicator values) from our dataset matching the sampling criteria. Indicator value analysis may now be performed for each individual indicator, i.e. measures of goodness may now be computed for the indicators to determine which indicators have differing values in a control state and a comparison state, and therefore, which indicators may give reliable information on the particular state. Indicator values may also be verified at this point to satisfy any assumptions, e.g. scalar indicators may be checked to be normally distributed (for example with Kolmogorov-Smirnov test). In addition, indicators whose sample data can't be tested for difference between states may at this point be eliminated from further analysis. Depending on the type of each indicator, measure of goodness computation may be done in different ways, as long as the result provides statistical information about the separation between the two groups.

One possibility to determine the measure of goodness is to use statistical tests (e.g. t-tests for scalar values and chi-square test of independence for nominal values). One of the control states and one of the comparison states are used in the statistical test. The result of the statistical test is a p-value that describes the probability that the differences in the indicator values between the control state and the comparison state are the result of chance alone. Therefore, the smaller the p-value the more probable it is that there are real differences in the indicator values between the control state and the comparison state. From the p-values of the i.sup.th indicators, p(i), the measure of goodness, S(i), may be computed for the indicators:

$$S(i) = \frac{\ln\min[p(i), 0.05] - \ln 0.05}{\ln 0.000001 - \ln 0.05}$$

The measure of goodness value S(i) is zero, if the p-value is larger than 0.05 (i.e., if there are no statistically significant differences in the control and comparison states), and it increases as the differences between the control and comparison states become larger. Alternatively, the measure of goodness could be the classification accuracy, computed e.g. using cross validation, when using the given indicator to classify control and comparison sample cases to control and comparison states. These methods for computing the measure of goodness are only examples and the computation could be implemented in many other ways.

By utilizing the sampled control and comparison states, in addition to measures of goodness, difference values may now be computed for the indicator values of the system of interest. These give information about the state of the system of interest in regards to individual indicator values obtained from the system of interest. Difference value computation can be done using e.g. distance measures or probabilistic measures.

A relative distance from the control state to the system of interest, when compared with the comparison state, may be calculated as:

$$d(i) = \frac{m(i) - \overline{m}_R(i)}{\overline{m}_S(i) - \overline{m}_R(i)}$$

where m(i) is the $i^{th}$ indicator of the system of interest, $\overline{m}_R$ (i) is the mean or median of the control state, and $\overline{m}_S$ (i) is the mean or median of the comparison state. The d(i) value shows how large the difference between the indicator value from the system of interest and the control state is, and which is the direction of the difference.

In a probabilistic measure, it is studied how the indicator values of the system of interest fit to the distributions of the corresponding indicators of the control and comparison states. Let us consider the case where $\overline{m}_R(i) < \overline{m}_S(i)$. The cumulative probabilities:

$$P_R(i) = P(m_R(i) \geq m(i))$$

and $$P_S(i) = P(m_S(i) \leq m(i))$$

are determined from the system data, where $m_R$ (i) and $m_S$ (i) denote the $i^{th}$ indicator values of the control and comparison states, respectively, $\overline{m}_R$ (i) is the mean or median of the control state, and $\overline{m}_S$ (i) is the mean or median of the comparison state. In other words, it is studied how probable it is that a system in the control state has a indicator value larger than the corresponding value of the system interest, and vice versa for the comparison state. The cumulative probabilities can be determined with any method, for example, using the Gaussian approximation or un-parametric methods. Alternatively, the normal probabilities, instead of cumulative probabilities could be used:

$$P_R(i) = P(m_R(i) \approx m(i))$$

and $$P_S(i) = P(m_S(i) \approx m(i))$$

A difference value for the indicator value m(i) of the system of interest may then be obtained from:

$$f(i) = \frac{P_S(i)}{P_S(i) + P_R(i)}$$

The difference value f(i) describes how well a indicator value m(i) of the system of interest fits to the distributions of the control and comparison states. The larger the value is the better the indicator value of the system of interest fits to the distribution of the comparison state. The difference value may obtain values between zero and 1. The value of 0.5 represents the case in which it is equally probable that the indicator value arises from a system having a state corresponding to the control state or to the comparison state.

In case $\overline{m}_R$ (i) > $m_S$ (i), the probabilities $P_R$ (i) = $P(m_R(i) \leq m$ (i)) and $P_S(i) = P(m_S(i) \geq m(i))$ are determined. Otherwise the analysis proceeds as presented above.

Difference values may be computed by using other methods than presented here. Other methods may produce a specific range of difference values or the difference values may be extrapolated after the fact so that values smaller than zero or difference values larger than 1 are possible.

For an example of measures of goodness and difference values, in our example dataset, we may find that delayed recall tests of the Mini Mental State Examination and volume of hippocampus computed from MRI images classify relatively well between healthy and AD patients in our control and comparison states, i.e. these indicators have a high measure of goodness. If difference values of these indicators in a patient show a high probability of AD, this information may be used to determine that the patient has high probability of actually having AD.

Figure 4A:
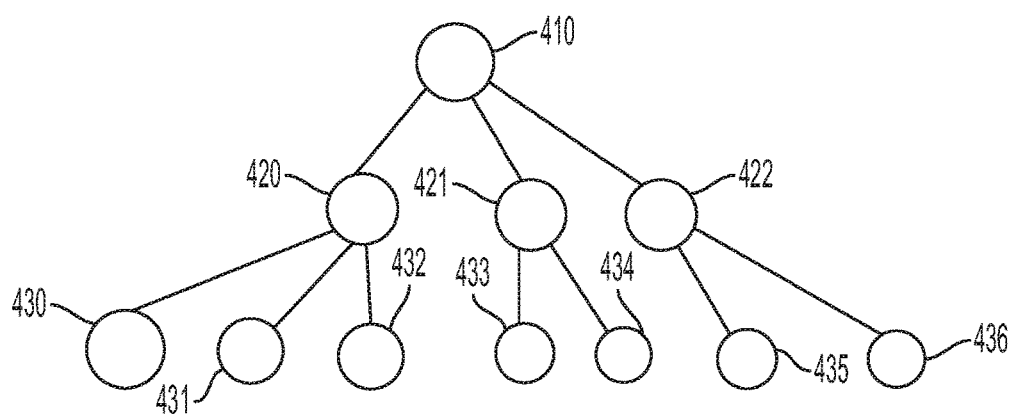
FIG. 4a illustrates propagation of the measures of goodness and/or the difference values in a tree-like representation of indicators according to an example embodiment.

FIG. 4a illustrates propagation of the measure of goodness and/or difference values in a tree-like representation of indicators according to an example embodiment. It has been noticed in the invention that data from an investigation can be logically structured into several categories and subcategories. There may be a number of different categories such as "Brain volumes", "Brain shapes", Hippocampus" and so on. An indicator or a composite indicator may belong to a number of categories. For example, the volume of the hippocampus could belong to categories "Brain volumes" and "Hippocampus". Here, it has been invented how to propagate the measures of goodness and/or difference values into parent nodes in a hierarchical tree. Measures of goodness and/or difference values from inside each category are grouped and a composite measure of goodness and/or difference value is computed for the parent node. As in FIGS. 3a and 3b, for example, all indicators from MMSE can be grouped into a composite MMSE node, which reveals the total measure of goodness in MMSE between the control and comparison systems and the total difference value of MMSE for the system of interest. Furthermore, MMSE, along with other neuropsychological tests can be grouped into single composite node, providing information about the total difference of all neuropsychological tests between the control and comparison systems and/or the system of interest. Propagating the results all the way up to the root node has a benefit of resulting in a full hierarchy of logically structured categories providing information about differences between the categories and an assessment of the system of interest's state at each level. The top level item may present e.g. a total difference value for the system of interest.

In FIG. 4a, the root node 410 has three child nodes 420, 421, 422. The root may have any number of child nodes of any kind. The child nodes may be intermediate nodes (composite indicators) such as in FIG. 4a, or they may be outer nodes (indicators) so that they do not themselves have any child nodes. In FIG. 4a, the root node 410 has 10 descendant nodes 420, 421, 422, 430, 431, 432, 433, 434, 435, 436. In FIG. 4a, the node 420 has in turn three child nodes 430, 431 and 432, and these child nodes are leaf nodes (indicators). The node 421 has two child nodes 433 and 434 and the node 422 has two child nodes 435 and 436. The nodes (indicators) may have a difference value or another value assigned to them implying to which state the system of interest belongs to. The nodes may also have a measure of goodness value assigned to them. The difference values and the measure of goodness values may be propagated from the leaf nodes to the intermediate nodes and further from the intermediate nodes to the root node. There may be any number of levels in the tree, and all the branches may be of same depth or they may be of different depth.

Figure 4B:
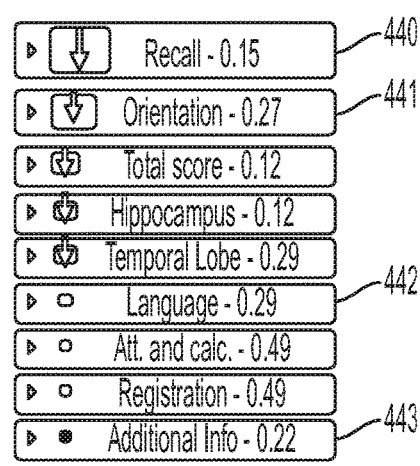
FIG. 4b illustrates ordering of the indicators according to the measure of goodness.

In FIG. 4b, the different indicators have been ordered according to their measure of goodness value (indicated by the size of the box). The most significant indicator is the Recall indicator 440, followed by the Orientation indicator 441. The Recall indicator also shows clearly that the system of interest is likely to belong to the normal state (it has a difference value of 0.15), whereas the Orientation feature has a larger difference value. The Language feature 442 and the Additional information feature 443 have a small classifying power, and they appear downwards in the representation from the more powerful indicators.

Reordering nodes based on the measure of goodness or difference value may be implemented with the following pseudo code:

```
FUNCTION reorder_nodes(LIST<NODE>nodes, ORDER order)
1: FOR EACH node IN nodes
2: reorder_node(node, nodes, order)
FUNCTION reorder_node(NODE node, LIST<NODE>nodes, ORDER order)
1: IF order=ORDER::GOODNESS
2:     var ordered_nodes=nodes.ORDER_BY_DESCENDING(n=>n.goodness))
3: ELSE IF order=ORDER::DIFFERENCE
4:     var ordered_nodes=nodes.ORDER_BY_DESCENDING(n=>n.difference))
5: VAR old_index=nodes.INDEX_OF(node);
6: VAR new_index=ordered_nodes.INDEX_OF(node);
7: IF (old_index !=new_index)
8: nodes.MOVE(oldIndex, newIndex);
```

In the code, node will be relocated in the list of nodes and nodes contains all the nodes of the same category, including the node to be relocated. Other ordering modes are also possible for implementation, for example ordering by increasing difference value.

Figure 4C:
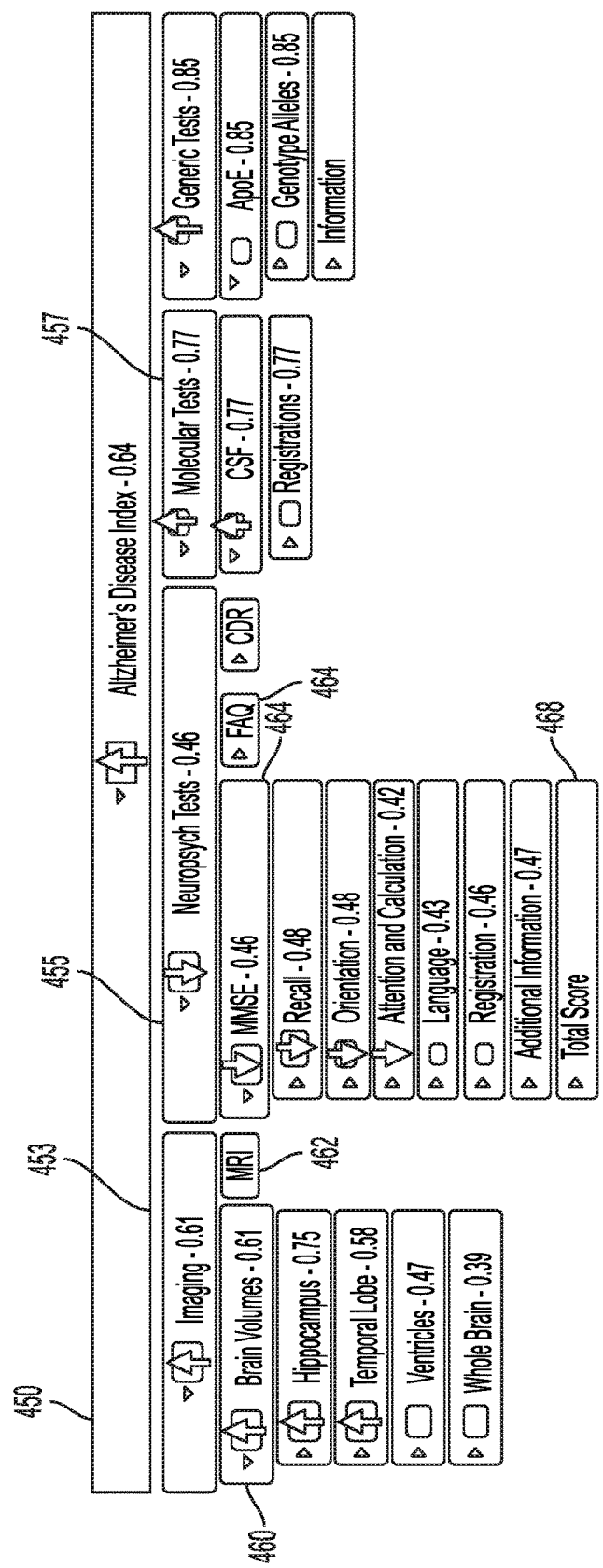
FIG. 4c illustrates refinement of the representation and visualization where indicators may be omitted from the state inference.

FIG. 4c illustrates refinement of the representation and visualization where indicators may be omitted from the state inference. In the user interface a user may be able to select which indicators are allowed to affect the analysis. This may be arranged by providing a means to remove an indicator node or a composite indicator node from the comparison and propagation phase. After a node has been removed, the composite difference and/or measure of goodness values may be computed again, ignoring any indicators that were removed. Any changes may immediately affect the visualization to make it reflect the updated state. This feature allows experts to focus on nodes they find interesting or deem important in making the final inference and/or classification.

In FIG. 4c, there is a visualization of a case where several composite nodes have been excluded from the computation. As shown earlier, there are a number of indicators below the top indicator 450. Some of these indicators like Imaging 453 and Molecular tests 457 indicate that a person would belong to the state of Alzheimer's disease, while some like Neuropsychological tests 455 indicate the normal state. Therefore, in the figure, neuropsychological tests suggest that the patient is healthy, while other evidence is indicating the opposite. Total difference value is leaning towards Alzheimer's disease due to more statistic significance (i.e. larger measure of goodness) from imaging, molecular tests and genetic tests combined. Some of the nodes are included in the computations and visualization like Brain Volumes 460 and MMSE 464, while others have been removed like MRI 462, CDR 464 and Total Score 468.

Computation of composite measures of goodness may be done with several methods and protocols. Measures of goodness from the child or descendant nodes or indicator values from child or descendant nodes may be used for the computation of composite measures of goodness. Methods for computing measures of goodness from child or descendant nodes include, among others: 1) selecting the largest measure of goodness; 2) using correct classification rate of control and comparison states as the measure of goodness; and 3) combining of indicator p-values. Several methods for computing a composite measure of goodness from child or descendant nodes are presented as pseudo code in the following. Composite measure of goodness could also be computed using other methods, not presented here.

In the maximum measure of goodness method, composite measure of goodness is chosen from the child or descendant node with the largest value, as indicated by the pseudo code below.

FUNCTION max_goodness(LIST<NODE>nodes)
RETURNS (goodness)
1: VAR goodness=nodes.MAXIMUM (node=>node.goodness)
2: RETURN (goodness)

Line one (1) selects the maximum value from measures of goodness in the nodes list, which is returned on line two (2).

In correct classification rate method, a combined difference value is computed with some method for each sample case in the control and comparison states. Using e.g. cross validation, these difference values are used for getting the correct classification rate (CCR) which is set as the measure of goodness for the composite indicator.

FUNCTION ccr_goodness(LIST<NODE>nodes)
RETURNS (goodness)
1: FOR EACH sample IN control_state, comparison state
2: diff[sample]=GET_COMPOSITE_DIFFERENCE (sample, nodes)
3: VAR goodness=GET_CORRECT_CLASSIFICATION_RATE (diff)
4: RETURN(goodness)

On line two (2) a method is called which computes a difference value for a sample from the control or comparison state, difference value computation methods are presented later. This method is called for each training sample due to the loop construct on line one (1). After all difference values for samples in the control and comparison states have been obtained, a method is called on line three (3) to compare them to correct classifications, known for the training set. Composite measure of goodness is then set as the correct classification rate.

In combined P method, the measure of goodness is computed from a weighted average of p-values that have been computed for child or descendant nodes. Weighting of the computation is obtained from difference values of the system of interest in the child or descendant nodes. The method may be implemented by combining the child or descendant nodes' underlying p-values with e.g. Stouffer's method. This is illustrated in the pseudo code below.

FUNCTION combine_p_goodness(LIST<NODE>nodes)
RETURNS (goodness)
1: VAR total_z=0
2: FOR EACH node IN nodes
3: VAR z=GET_Z_SCORE(node.p_value)
4: total_z+=(node.difference−0.5)*z
5: total_z/=SQRT(nodes.SUM(node=>(node.difference−0.5)^2))
6: VAR goodness=GET_GOODNESS_FROM_P(GET_P_VALUE(total_z))
7: RETURN (goodness)

On line three (3), p values of indicators are converted to z scores, which are weighted by the node difference on line 4 and added to a total z score, as defined in Stouffer's method. Combined z score is obtained by dividing the total weighted z score by the square root of the sum of squared weights, which is then converted to a p value and used for getting the measure of goodness, using e.g. method presented on page 9.

Logistic regression and principal component analysis (PCA) may also be used in the propagation of measure of goodness values to composite indicators. Instead of using all indicators from child or descendant nodes, a PCA projection is used to find indicators which define the composite indicator well. The measure of goodness is then determined e.g. by using logistic regression to evaluate the PCA projections' ability to classify sample cases from control and comparison states, as shown in pseudo code below.

FUNCTION pca_log_reg(LIST<NODE>nodes)
RETURNS (goodness)
1: VAR pca=PCA(nodes.control, nodes.comparison)
2: VAR diff=LOG_REG(pca, nodes.control, nodes.comparison)
3: VAR goodness=GET_CORRECT_CLASSIFICATION_RATE (diff)
4: RETURN (goodness)

First, a PCA projection from the indicators is obtained on line one (1). Difference values are computed for the samples in control and comparison states on line two (2) using this time logistic regression. After all difference values for samples in the control and comparison states have been obtained, a method is called on line three (3) to compare them to correct classifications, known for the training set. Composite measure of goodness is then set as the correct classification rate.

As was the case with composite measures of goodness, composite difference values may also be computed using several methods. It should be noted that composite indicator values for control and comparison states or for the system of interest are not necessarily computed, since it may be impossible to combine multiple indicator values to a single composite indicator value in a sensible manner. Another matter to observe is that composite difference values computed using the methods presented below are conceptually different from difference value computation methods presented earlier. Previously presented difference value computation methods (using indicator values) may be applied to the results from composite difference value computation methods to get composite difference values conceptually identical to difference values computed from the indicator values.

Composite difference values can be computed with e.g. weighted averaging, in which the indicator difference values are averaged with weightings that are the measures of goodness:

$$D = \frac{\sum_i S(i) f(i)}{\sum_i S(i)}$$

The obtained value D describes how closely the indicator values of the system of interest match with the corresponding values in the comparison state. Logistic regression (sometimes called the logistic model or logit model) can also be used for prediction of the probability that the system of interest fits comparison system by fitting indicator values to a logistic curve, providing a composite difference value for the system of interest.

Composite difference may also be derived by first computing a difference value for the system of interest as defined above and then also computing difference values for all samples in the control and comparison states using the same method. Using the difference value of the system of interest, we can now compute a composite difference value from the normal or cumulative probability against difference values from control and control states using the same methods that were presented for computing difference values from indicator values starting from page 10. Again, as with composite measures of goodness, the methods presented here for computing composite differences are not exhaustive, but other methods could also be used.

From tables containing numerical data of the indicators, measures of goodness, and difference values it may be difficult to perceive the most important differences between the different states or to compare a system of interest with the different states. On the other hand, the human visual system can effectively process information coded with colours and shapes and sizes of objects. Still, if there is a high amount of data coded with colours and shapes and sizes, it has been noticed in the invention that the human visual system may get dis-oriented. Therefore, a tree structure for visualizing data such as in FIGS. 5a and 5b has been invented. FIGS. 5a, 5b, 5c and 5d show representations and visualizations of indicators in a grouped tree structure according to an example embodiment of the invention for different systems. The visualization method may be explained by an example of an analysis support system for Alzheimer's disease. The system of interest we may want to infer is whether a person has or will develop Alzheimer's disease. From medical records databases, two states may be created based on those who are healthy and those who have developed Alzheimer's disease. They are analyzed using the methods presented in this invention and the patient in question is compared to both states as defined in this invention.

Figure 5A:
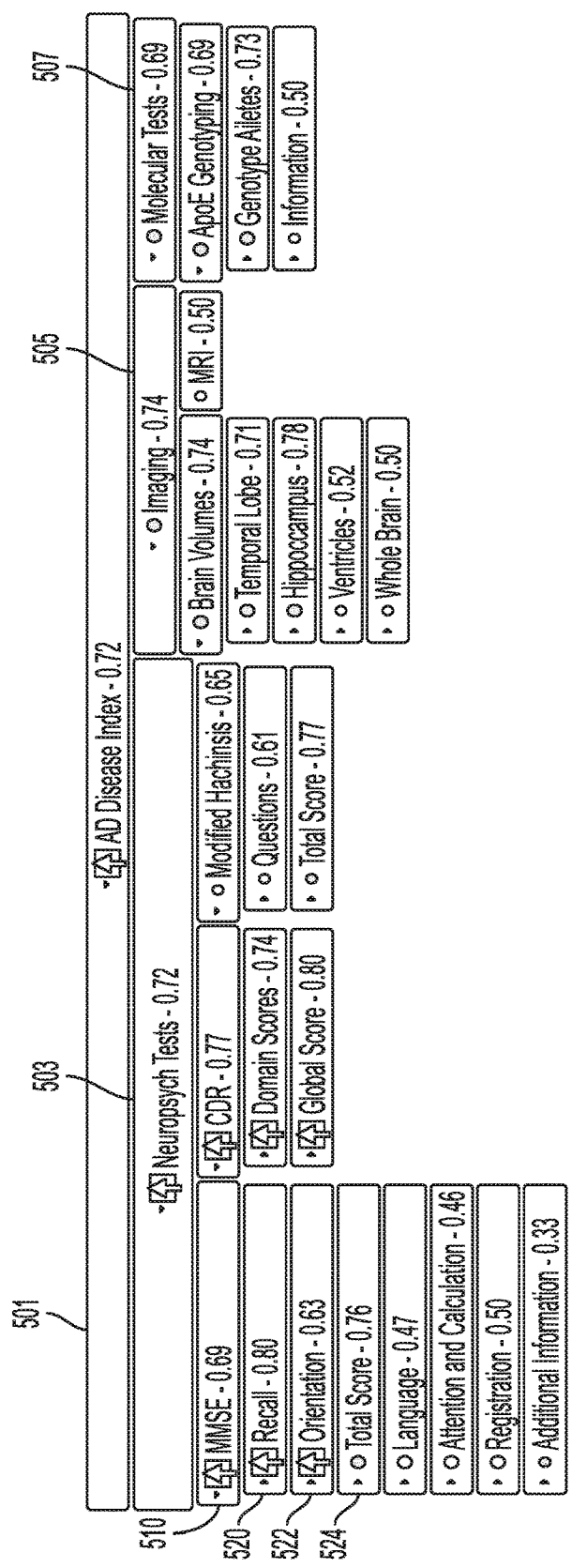
FIGS. 5a, 5b, 5c and 5d show representations and visualizations of indicators in a grouped and sorted tree structure according to an example embodiment of the invention for different systems.

FIG. 5a shows a representation of a person with high probability of having or developing Alzheimer's disease. Some characteristics of our visualization method are presented in the following. The box size may be used to show statistical significance differentiating the two groups, that is, the box size may show the measure of goodness. The state of the system of interest (the person) may be shown with colours and difference values indicating whether the patient matches either of the groups (Blue/0—Healthy, White/0.5—Undecided, Red/1—Alzheimer's disease). Blue colour (in the figures highlighted with an arrow pointing down) may be used when the indicator value of the system of interest or the comparison state is smaller than the corresponding indicator value of the control state, and red colour (in the figures highlighted with an arrow pointing up) is used when the corresponding indicator value of the system of interest or control state is larger. The colours may be chosen so that a colour-blind person may easily be able to separate them. The darker the shade of the colour used is, the bigger the difference in relation to the control state (in the figure, the size of the arrow refers to the shade of the colour). Tree hierarchy may be used to organize heterogeneous indicators according to their type and category. The composite difference values and the composite measures of goodness for the different indicators of the intermediate nodes are computed from child nodes and may be propagated in the tree towards the root node. Indicating the difference values and measures of goodness in the visualization can also be done in different manners instead of the one presented in the figures. Thumbnail images may be rendered next to each node to reveal the distributions of indicator values in control and comparison states from which measures of goodness are computed. In the images a marker may be also be rendered to reveal indicator values from the system of interest to see their values in relation to the distributions. Pointers may be used so that the orientations of the pointers are used to visualize the differences in the indicator values between the system of interest or the comparison state and the control state: a pointer pointing up shows that the indicator value of the system of interest or the comparison state is larger than the corresponding indicator value of the control state, and vice versa for the pointers pointing down. The size of the pointer may change in proportion to the measure of goodness determined for the indicator. Alternatively or additionally, the visualization tool may show difference values in a figure with the measures of goodness. The difference values may be represented as bars extending from the value 0.0 to the calculated value of the difference value on a scale from 0.0 to 1.0. The measures of goodness may be represented by a line graph in a two-dimensional, orthogonal axis system e.g. such as shown in FIG. 3.

In FIG. 5a, it can be seen that all modalities of the AD Disease Index 501 (neuropsychological tests 503, imaging data 505, and molecular tests 507) indicate that the person has or will have Alzheimer's disease. In addition, due to box sizes it can be seen that the most significant indicators are inside the 'Recall' category 520 from 'MMSE' (Mini Mental State Examination) 510 and that the information is fairly reliable (large box size indicating a large measure of goodness). The 'Recall' category, 'Orientation' 522 and 'Total Score' 524 are the indicators with the highest measure of goodness.

Figure 5B:
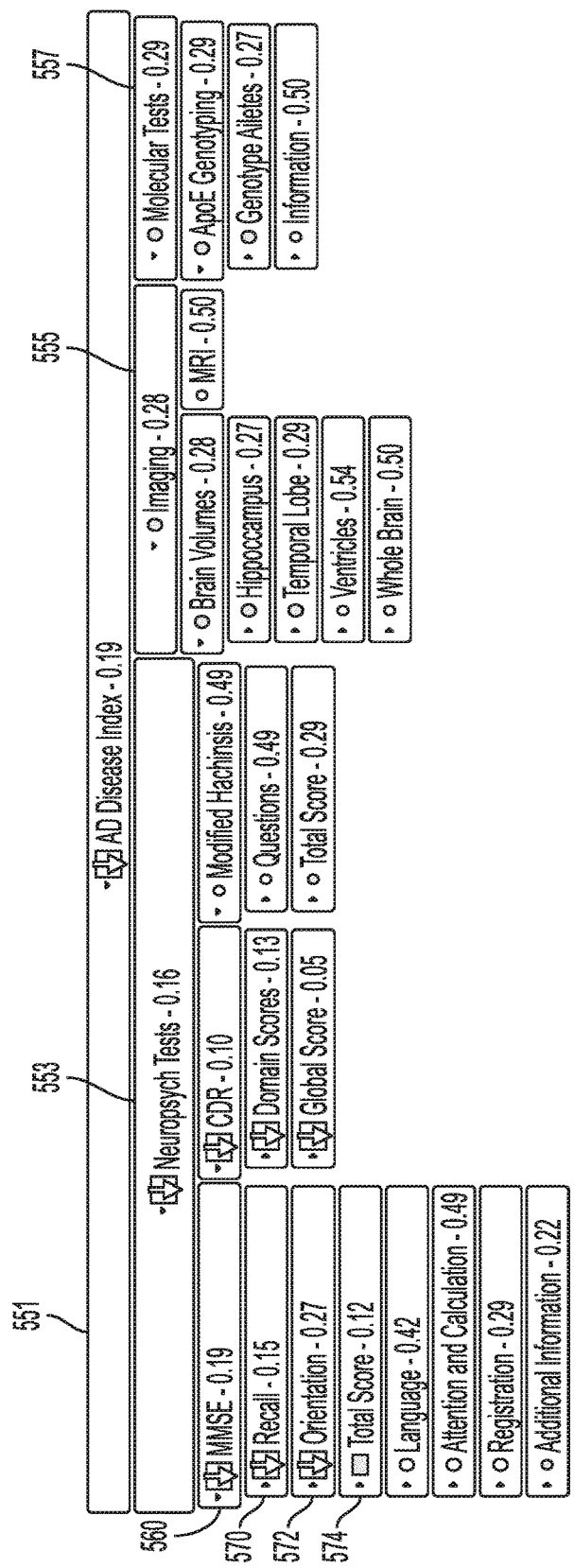

In FIG. 5b, there is the same analysis as in FIG. 5a, but now the analysis is for a healthy person. It may be seen from the difference values that the person is in healthy state and the box size shows that this is reliable information. The different modalities of the AD Disease Index 551 (neuropsychological tests 553, imaging data 555, and molecular tests 557) all indicate a healthy state. The most prominent indicators by measure of goodness (largest box) are the MMSE category 560, inside MMSE the 'Recall' 570 indicator, the 'Orientation' indicator 572 and the 'Total Score' indicator 574 have the highest measure of goodness.

In addition to grouping by category, the tree structure may be organized according to e.g. measure of goodness so that the most significant data appear visually together. For example, the indicators may be arranged in descending order of the measure of goodness and then displayed so that the indicators with the highest measures of goodness are in one corner of the tree representation. In FIGS. 5a and 5b, the most significant indicators are in the upper left part of the tree, but they may be in the middle in a network representation, or in any other corner, or in some other way grouped visually together. In the visualization, the nodes may be re-ordered vertically or horizontally to show the most significant indicators e.g. from top to bottom and left to right. Applying this re-ordering allows presenting a visualization where the most important items can be read at one glance for example at the top and left towards down and right. This is exemplified in FIGS. 5a and 5b, as well as 4c, where Neuropsychological tests, Imaging, and Genetic tests are each in their own categories, with the most important coming first horizontally/vertically (Neuropsychological tests/MMSE) and the less important later (Imaging and Genetic tests). FIG. 5b also illustrates ordering of the indicators according to the measure of goodness. Instead of random or structural ordering of the compared indicators, the indicators may be ordered for visualization according to the significance of each indicator. That is, indicators with more classifying power can be visualized with a bigger box or arrow at the top of a list of indicators. With colors or arrow directions indicating differences between states, this visualization may offer a better system overview at a quick glance than arbitrary ordering. In addition, a system of interest may be compared to each of the control and comparison states and from that several composite difference values can be computed and the colors can instead be rendered indicating which control or comparison state the system of interest best fits.

Figure 5C:
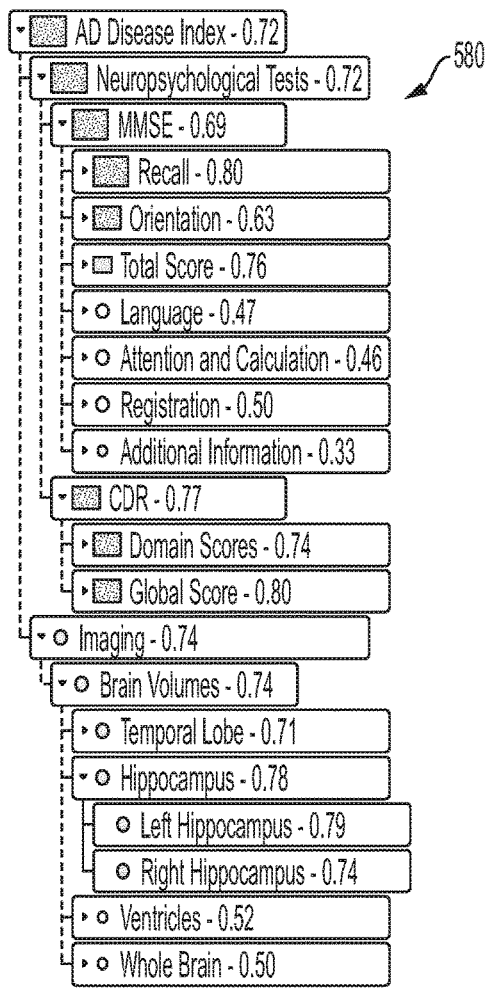
Figure 5D:
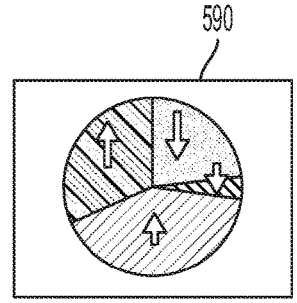

In FIG. 5c, the different indicators have been organized as a vertical tree 580, where the grouping of the indicators has been done as before, but the level of the indicator is shown as indentation. In this representation, the values in the group with the largest measure of goodness may be shown first. However, in the vertical direction, there may be indicator values with smaller measure of goodness above indicator values with larger measure of goodness due to the collapsed nature of the tree. In FIG. 5d, the visualization has been done with the help of a pie chart, where the measure of goodness determines the size of the pie, and the difference value determines the colour. With this representation, the human visual system may easily detect which state the system is in from the dominance of the colours on the pie chart. The depth of the colours may be indicated the reliability of the information.

Figure 6A:
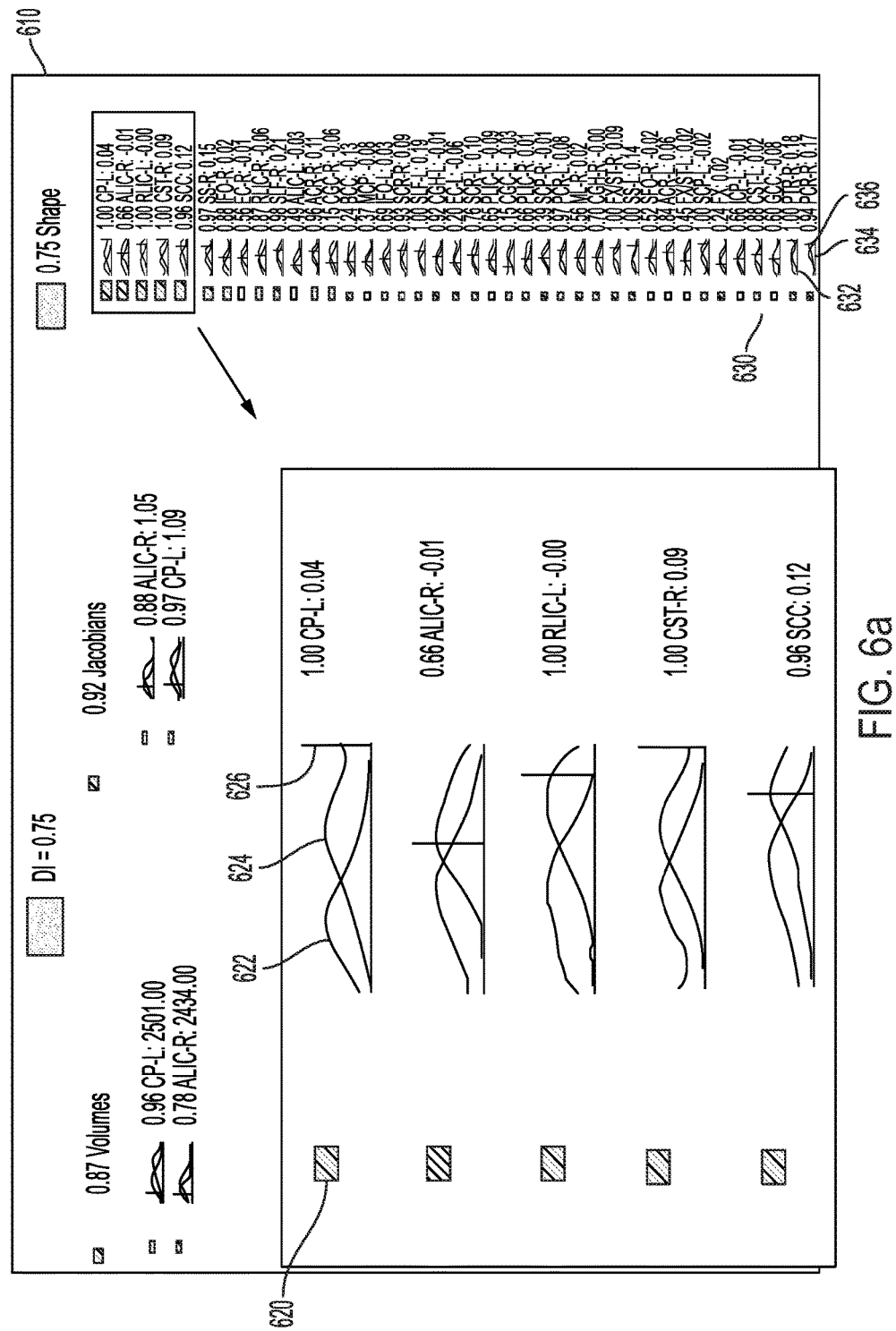
FIGS. 6a and 6b show the use of statistical distribution functions in visualizing the measure of goodness and the difference value.
Figure 6B:
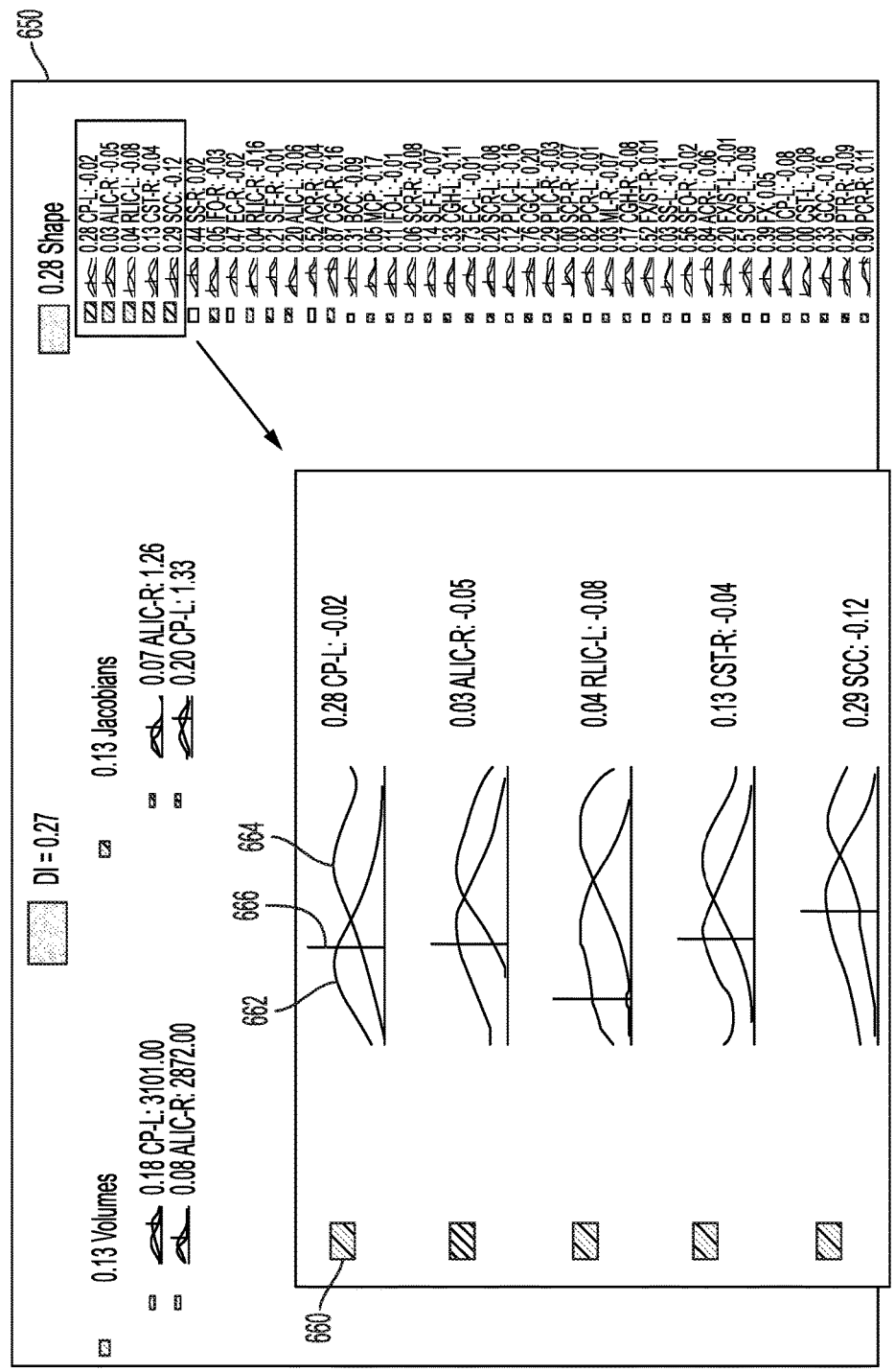

FIGS. 6a and 6b show the use of statistical distribution functions in visualizing the measure of goodness and the difference value. In FIG. 6a, the distributions of the indicator values related to a certain state and a comparison state are shown in a display 610. As before, the measure of goodness is shown with the size of the box 620, while the difference value is shown with the (shade of) color of the box 620. In the distribution plot, the normal state 622 and disease state 624 distributions for an indicator value are shown. For this indicator, the difference value if the system of interest is 1.0, and the indicator shows that the system is in the disease state. For an indicator 630 with a smaller measure of goodness, the curves 632 and 634 of the two states overlap more, and the information given by the indicator value 636 of the system of interest is not as reliable. Correspondingly in the display 650 of FIG. 6b, the box 660 indicates a healthy state, with the curves 662 and 664 showing a high measure of goodness (low overlap) and the difference value indicating the healthy state.

Figure 7:
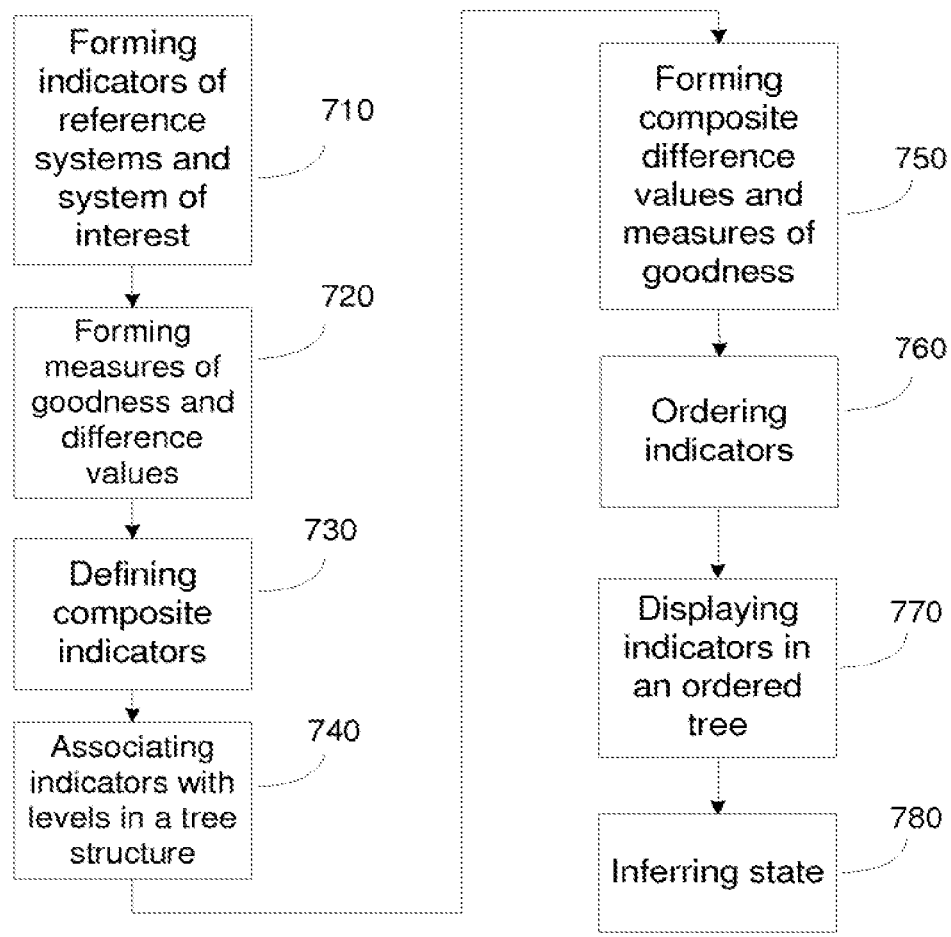
FIG. 7 illustrates a method according to an embodiment for inferring the state of a system of interest according to an example embodiment.

FIG. 7 illustrates a method according to an embodiment for inferring the state of a system according to an example embodiment. In phase 710, indicators of the control and comparison states and the system of interest are formed, as described earlier. In phase 720, the measures of goodness and the difference values are formed for the indicators, e.g. by statistical measures as described in context of FIG. 4. In phase 730, the composite indicators are defined, e.g. by grouping according to the content of the indicators and arranging the leaf indicators to be children of composite indicators, as described in context of FIG. 5a. Then, in phase 740, the indicators may be arranged to different levels in a tree structure. In phase 750, composite difference values and the composite measures of goodness are formed, as described earlier. The indicators may then be re-ordered in phase 760, e.g. according to the measure of goodness values. In phase 770, the indicators may be displayed to the user in a tree structure, and the user may also manipulate the tree structure as described. In phase 780, the state may be inferred by the system, by the user or by both.

The above-mentioned methods to compute the measures of goodness and the difference values non-restrictive examples of possible methods that can be used. Any method related to the presented methods can be used as well.

In addition to studying the state of a system of interest, the proposed method can be utilized in classifying a system of interest. This can be carried out by comparing the data of the system of interest with different control and comparison states. Then the results obtained for the different control and comparison states, i.e. the values of the measure of goodness, the difference values or fitness values, and the state indicators, may be compared and the system of interest is classified as the state that is the most similar to the system of interest.

It is obvious that the present invention is not limited solely to the above-presented embodiments, but it can be modified within the scope of the appended claims.

What is claimed:

1. A computer-implemented method in an apparatus for inferring a state of a system of interest, the system of interest being a human body, the method comprising the steps of:

defining, via a processor, a first medical measurement value for a first indicator and a second medical measurement value for a second indicator in the human body, where the first medical measurement value and the second medical measurement value are indicative of the state of the system of interest;

retrieving first medical database values for the first indicator and second medical database values for the second indicator, wherein the first medical database values include values of at least one example of a system that is known to be in a control state and at least one example of a system that is known to be in a comparison state, and wherein the second medical database values include values of at least one example of a system that is known to be in a control state and at least one example of a system that is known to be in a comparison state;

determining, via said processor, a first measure of goodness for said first indicator by applying a statistical test to said first medical database values and a second measure of goodness for said second indicator by applying a statistical test to said second medical database values, said first measure of goodness for said first indicator and said second measure of goodness for said second indicator indicating how significant said first indicator and said second indicator are statistically in differentiating between said control state and said comparison state;

determining, via said processor, a first difference value for said first medical measurement value and a second difference value for said second medical measurement value, said difference value for said first medical measurement value and said difference value for said second medical measurement value indicating a relative distance of said first medical measurement value and said second medical measurement value from said control state when compared with said comparison state;

defining, via said processor, a composite difference value describing how closely the first medical measurement value and the second medical measurement value match with the corresponding medical database values of at least one of the comparison state or the control state;

determining, via said processor, a composite measure of goodness for the composite difference value by using information indicative of said first measure of goodness for said first indicator and said second measure of goodness for said second indicator, said composite measure of goodness for the composite difference value indicating how significant said composite difference value is statistically in differentiating between said control state and said comparison state;

forming, via said processor, an initial tree structure comprising a plurality of nodes, said plurality of nodes being indicative of said first and second medical measurement values and one or more of the first and second difference values and being based upon at least said composite difference value and said composite measure of goodness;

automatically re-ordering, via said processor, one or more of said plurality of nodes in said initial tree structure based on relative values of the measures of goodness or the difference values, said re-ordering resulting in a reordered tree structure;

generating, via said processor, a visualization of at least said reordered tree structure for a user of said apparatus, said visualization being interactively accessible to said user via a user interface for interactive inferring a state of a system of interest; and dynamically refining, via said processor, said reordered tree structure, said dynamic refining occurring in response to one or more interactive user selections related to said first and second measurement values and one or more difference values.

2. A method according to claim 1, further comprising the step of:

displaying, via said processor, said difference values arranged in an order according to their respective measures of goodness for inferring the state of the system of interest.

3. A method according to claim 1, further comprising the step of displaying said difference values of said first measurement value and for said second measurement value, wherein:

said difference values are displayed with a value, said value being selected from the group consisting of: a number, a symbol, a color, a shade, a pattern, a bar or a gauge; and said difference values are at least one of highlighted or suppressed according to the respective measure of goodness of said first indicator, for said second indicator, and for said composite difference value using a visual cue selected from the group consisting of: size, blinking, position on the display, or stacking.

4. A method according to claim 1, further comprising the steps of:

determining, via said processor, a total difference value for the system of interest, said total difference value indicating a relative distance of the system of interest from said control state when compared with said comparison state;

displaying, via said processor and a display, said total difference value for said system of interest with a colour symbol on a first level in said tree structure;

displaying, via said processor and a display, said difference value for said first measurement value and said difference value for said second measurement value with a colour symbol on a second level in said tree structure;

displaying, via said processor and on a display, said measures of goodness for said first indicator, for said second indicator, and for said composite difference value with a size of said colour symbol.

5. A method according to claim 4, further comprising the steps of:

grouping, via said processor, said tree structure by forming groups of indicators that are on the same level of the tree and that are linked to a composite difference value of another level; and arranging, via said processor, said groups of said tree structure according to said measures of goodness so that indicators having a larger measure of goodness are arranged to appear visually together.

6. A method according to claim 5, further comprising the steps of:

arranging, via said processor, said groups of indicators to appear horizontally in a decreasing order according to the respective measures of goodness of the composite difference values; and arranging, via said processor, indicators inside said groups of indicators to appear vertically in a decreasing order according to their respective measures of goodness.

7. A method according to claim 1, further comprising the step of:

calculating, via said processor, a total difference value for said system of interest from the difference values of said first measurement value and of said second measurement value, the calculation comprising averaging with weightings that are the respective measures of goodness of said first and of said second indicator.

8. A method according to claim 1, further comprising the step of:

calculating, via said processor, the measures of goodness of said first indicator, of said second indicator, and of said composite difference value by determining a statistical probability of said indicator and of said composite difference value, said probability being a reliable measure for determining whether the said system of interest belongs to said at least one control or comparison state.

9. A method according to claim 1, further comprising the step of:

calculating, via said processor, the measure of goodness of said composite difference value using attributes of said first and second indicators of said system of interest in the calculation.

10. A method according to claim 1, further comprising the step of:

calculating, via said processor, at least one of said difference values by comparing measurement values for an indicator of said system of interest to database values for the indicators of at least one control and comparison state; and calculating, via said processor, at least one of said measures of goodness by using a statistical distribution of said at least one control and comparison state.

11. An apparatus for inferring a state of a system of interest, the system of interest being a human body, said apparatus comprising:

at least one processor and memory comprising computer program code, the memory and the computer program code configured to, with the at least one processor, cause the apparatus to:

determine a first medical measurement value for a first indicator and a second medical measurement value for a second indicator in the human body, where the first medical measurement value and the second medical measurement value are indicative of the state of the system of interest;

retrieve first medical database values for the first indicator and second medical database values for the second indicator, wherein the first medical database values include values of at least one example of a system that is known to be in a control state and at least one example of a system that is known to be in a comparison state and wherein the second medical database values include values of at least one example of a system that is known to be in a control state and at least one example of a system that is known to be in a comparison state;

determine a measure of goodness for said first indicator by applying a statistical test to said first medical database values and determine a measure of goodness for said second indicator by applying a statistical test to said second medical database values, said measure of goodness for said first indicator and said measure of goodness for said second indicator indicating how significant said first indicator and said second indicator are statistically in differentiating between said control state and said comparison state;

determine a difference value for said first medical measurement value and determine a difference value for said second medical measurement value, said difference value for said first medical measurement value and said difference value for said medical second measurement value indicating a relative distance of said first medical measurement value and said second medical measurement value from said control state when compared with said comparison state;

define a composite difference value describing how closely the first medical measurement value and the second medical measurement value match with the corresponding medical database values of at least one of the comparison state or the control state;

determine a composite measure of goodness for the composite difference value by using information indicative of said measure of goodness of said first indicator and said measure of goodness for said second indicator, said composite measure of goodness for the composite difference value indicating how significant said composite difference value is statistically in differentiating between said control state and said comparison state;

form an initial tree structure comprising a plurality of nodes, said plurality of nodes being indicative of said first and second medical measurement values and one or more of the first and second difference values and being based upon at least said composite difference value and said composite measure of goodness;

automatically re-order one or more of said plurality of nodes in said initial tree structure based on relative values of the measures of goodness or the difference values, said re-ordering resulting in a reordered tree structure;

generate a visualization of at least said reordered tree structure for a user of said apparatus, said visualization being interactively accessible to said user via a user interface and configured for interactively inferring a state of a system of interest; and dynamically refine said reordered tree structure said dynamic refining occurring in response to one or more interactive user selections related to said first and second measurement values and one or more difference values.

12. An apparatus according to claim 11, further comprising computer program code configured to, with the at least one processor, cause the apparatus to:

display difference values arranged according to their respective measures of goodness for inferring the state of the system of interest.

13. An apparatus according to claim 11, further comprising computer program code configured to, with the processor, cause the apparatus to:

display said difference values of said first measurement value and for said second measurement value, wherein:
said difference values are displayed with a value being selected from the group consisting of: a number, a symbol, a color, a shade, a pattern, a bar or a gauge; and
said difference values are at least one of highlighted or suppressed according to the respective measure of goodness of said first indicator, for said second indicator, and for said composite difference value using a visual cue selected from the group consisting of:
size, blinking, position on the display, or stacking.

14. An apparatus according to claim 11, further comprising computer program code configured to, with the processor, cause the apparatus to:

determine a total difference value for the system of interest, said total difference value indicating a relative distance of the system of interest from said control state when compared with said comparison state;

display said total difference value of said system of interest with a colour symbol on a first level in said tree structure;

display said difference value for said first measurement value and said difference value for said second measurement value with a colour symbol on a second level in said tree structure; and display said measures of goodness for said first indicator, for said second indicator, and for said composite difference value with a size of said colour symbol.

15. An apparatus according to claim 14, further comprising computer program code configured to, with the processor, cause the apparatus to:

group said tree structure by forming groups of indicators that are on the same level of the tree and that are linked to a composite difference value of another level; and arrange said groups of said tree structure according to said measures of goodness so that indicators having a larger measure of goodness are arranged to appear visually together.

16. An apparatus according to claim 15, further comprising computer program code configured to, with the processor, cause the apparatus to:

arrange said groups of indicators to appear horizontally in a decreasing order according to the respective measures of goodness of the composite difference values; and arrange indicators inside said groups of indicators to appear vertically in a decreasing order according to their respective measures of goodness.

17. An apparatus according to claim 11, further comprising computer program code configured to, with the processor, cause the apparatus to:

compute a total difference value for said system of interest from the difference values of said first measurement value and of said second measurement value the calculation comprising averaging with weightings that are the respective measures of goodness of said first and of said second indicator.

18. An apparatus according to claim 11, further comprising computer program code configured to, with the processor, cause the apparatus to:

compute the measures of goodness of said first indicator, of said second indicator, and of said composite difference value by determining a statistical probability of said indicator and of said composite difference value, said probability being a reliable measure for determining whether the said system of interest belongs to said at least one control or comparison state.

19. An apparatus according to claim 11, further comprising computer program code configured to, with the processor, cause the apparatus to:
compute the measure of goodness of said composite difference value using attributes of said first and second indicators of said system of interest in the calculation.

20. An apparatus according to claim 11, further comprising computer program code configured to, with the processor, cause the apparatus to:
compute at least one said difference value by comparing measurement values for an indicator of said system of interest to database values for the indicators of at least one control and comparison state; and
compute at least one said measure of goodness by using a statistical distribution of said at least one control and comparison state.

21. A system for inferring a state of a system of interest, the system of interest being a human body, the system comprising at least one processor, memory including computer program code, the memory and the computer program code configured to, with the at least one processor, cause the system to:
determine a first medical measurement value for a first indicator and a second medical measurement value for a second indicator in human body, where the first medical measurement value and the second medical measurement value are indicative of the state of the system of interest;
retrieve first medical database values for the first indicator and second medical database values for the second indicator, wherein the first medical database values include values of at least one example of a system that is known to be in a control state and at least one example of a system that is known to be in a comparison state and wherein the second medical database values include values of at least one example of a system that is known to be in a control state and at least one example of a system that is known to be in a comparison state;
determine a measure of goodness for said first indicator by applying a statistical test to said first medical database values and determine a measure of goodness for said second indicator by applying a statistical test to said second medical database values, said measure of goodness for said first indicator and said measure of goodness for said second indicator indicating how significant said first indicator and said second indicator are statistically in differentiating between said control state and said comparison state;
determine a difference value for said first medical measurement value and determine a difference value for said second medical measurement value, said difference value for said first medical measurement value and said difference value for said second medical measurement value indicating a relative distance distance of said first medical measurement value and said second medical measurement value from said control state when compared with said comparison state;
define a composite difference value describing how closely the first medical measurement value and the second medical measurement value match with the corresponding medical database values of at least one of the comparison state or the control state;
determine a composite measure of goodness for the composite difference value by using information indicative of said measure of goodness of said first indicator and said measure of goodness for said second indicator, said composite measure of goodness for the composite difference value indicating how significant said composite difference value is statistically in differentiating between said control state and said comparison state;
form an initial tree structure comprising a plurality of nodes, said plurality of nodes being indicative of said first and second medical measurement values and one or more of the first and second difference values and being based upon at least said composite difference value and said composite measure of goodness;
re-order one or more of said plurality of nodes in said initial tree structure based on relative values of the measures of goodness or the difference values, said re-ordering resulting in a reordered tree structure;
generate a visualization of at least said reordered tree structure for a user of said apparatus, said visualization being interactively accessible to said user via a user interface and configured for interactively inferring a state of a system of interest; and
dynamically refine said reordered tree structure said dynamic refining occurring in response to one or more interactive user selections related to said first and second measurement values and one or more difference values.

22. A system according to claim 21, further comprising computer program code configured to, with the processor, cause the system to:
display difference values arranged according to their respective measures of goodness for inferring the state of the system of interest.

23. A computer program product for inferring a state of a system of interest, said system of interest being a human body, said computer program product being stored on a non-transitory computer readable medium and executable in a data processing device, the computer program product comprising one or more computer program code sections configured for:
determining a first medical measurement value for a first indicator and a second medical measurement value for a second indicator in the human body, where the first medical measurement value and the second medical measurement value are indicative of the state of the system of interest,
retrieving first medical database values for the first indicator and second medical database values for the second indicator, wherein the first medical database values include values of at least one example of a system that is known to be in a control state and at least one example of a system that is known to be in a comparison state and wherein the second medical database values include values of at least one example of a system that is known to be in a control state and at least one example of a system that is known to be in a comparison state;
determining a measure of goodness for said first indicator by applying a statistical test to said first medical database values and determining a measure of goodness for said second indicator by applying a statistical test to said second medical database values, said measure of goodness for said first indicator and said measure of goodness for said second indicator indicating how significant said first indicator and said second indicator are statistically in differentiating between said control state and said comparison state, determining a difference value for said first medical measurement value and determining a difference value for said second medical measurement value, said difference value for said first medical measurement value and said difference value for said second medical measurement value indicating a relative distance of said first medical measurement value and said second medical measurement value from said control state when compared with said comparison state, defining a composite difference value describing how closely the first medical measurement value and the second medical measurement value match with the corresponding medical database values of the comparison state and/or the control state, determining a composite measure of goodness for the composite difference value by using information indicative of said measure of goodness for said first indicator and said measure of goodness for said second indicator, said composite measure of goodness for the composite difference value indicating how significant said composite difference value is statistically in differentiating between said control state and said comparison state, forming an initial tree structure comprising a plurality of nodes, said plurality of nodes being indicative of said first and second medical measurement values and one or more of the first and second difference values and being based upon at least said composite difference value and said composite measure of goodness, automatically re-ordering one or more of said plurality of nodes in said initial tree structure based on relative values of the measures of goodness or the difference values, said re-ordering resulting in a reordered tree structure;

generating a visualization of at least said reordered tree structure for a user of said apparatus, said visualization being interactively accessible to said user via a user interface and configured for interactively inferring a state of a system of interest; and dynamically refining said reordered tree structure said dynamic refining occurring in response to one or more interactive user selections related to said first and second measurement values and one or more difference values.

24. A computer program product according to claim 23, wherein the one or more computer program code sections are further configured for:

displaying difference values arranged according to their respective measures of goodness for inferring the state of the system of interest.

* * * * *